United States Patent
Rose

(10) Patent No.: US 10,375,892 B2
(45) Date of Patent: Aug. 13, 2019

(54) PROCESS FOR PURIFYING GLANDULAR TRICHOMES

(71) Applicant: Mark Jeffery Rose, Golden, CO (US)

(72) Inventor: Mark Jeffery Rose, Golden, CO (US)

( * ) Notice: Subject to any disclaimer, the term of this patent is extended or adjusted under 35 U.S.C. 154(b) by 333 days.

(21) Appl. No.: 15/202,357

(22) Filed: Jul. 5, 2016

(65) Prior Publication Data

US 2018/0007852 A1    Jan. 11, 2018

(51) Int. Cl.
*A01D 91/00* (2006.01)
*A61K 36/185* (2006.01)

(52) U.S. Cl.
CPC ............ *A01D 91/00* (2013.01); *A61K 36/185* (2013.01); *A61K 2236/00* (2013.01)

(58) Field of Classification Search
None
See application file for complete search history.

(56) References Cited

U.S. PATENT DOCUMENTS 6,158,591 A    12/2000   Delp
2013/0079531 A1    3/2013    Barringer

OTHER PUBLICATIONS

Amme et al , Proteomics 5: 2508-2518 (Year: 2005).*
Hashidoko et al, Plant Cell and Physiology 36(1): 127-132 (Year: 1995).*
Happyana et al, Phytochemistry 87: 51-59 (Year: 2013).*
Yerger et al, Plant Physiology 99: 1-7 (Year: 1992).*
Yerger et al., A Rapid Method for Isolating Glandular Trichomes, Plant Physiol, 1992, 99, 1-7.

* cited by examiner

*Primary Examiner* — David H Kruse
(74) *Attorney, Agent, or Firm* — Haug Partners LLP

(57) ABSTRACT

The present invention relates to a dry process for isolating clean glandular trichomes from a trichome bearing plant material, wherein the trichome bearing plant material is frozen at −20° C. and subject to shattering and softening sequence.

8 Claims, No Drawings

PROCESS FOR PURIFYING GLANDULAR TRICHOMES

FIELD OF THE INVENTION

This disclosure relates generally to the production of purified glandular trichomes, and more specifically to the production of purified trichomes resin from *Cannabis sativa* plants.

BACKGROUND

Most plants have specialized hair-like trichome structures on leaf surfaces, non-glandular trichomes being very common, glandular trichomes being less common. Glandular trichomes are capable of storing relatively large amounts of secondary metabolites, like terpenoids, as part of the essential oil of the plant, making them a target for the production of valuable small molecules.

For example, peppermint oil, consisting primarily of monoterpenes and minor quantities of sesquiterpenes is synthesized and accumulated in specialized peltate glandular trichomes of the peppermint plant and finds use as a flavor in numerous consumer products (e.g., chewing gum, mouthwash . . . ) in the confectionary and pharmaceutical industries.

Whereas since the distant past, 8000 B.C. up the present, *Cannabis* in various forms was either eaten or smoked, the major usage being a recreational drug all over the world, cannabinoids and their derivatives were the mainstay of early medicine and the seeds were integrated into most every cuisine around the world, *Cannabis* products have been consumed in various forms for thousands of years. Descriptions of medical uses in Chinese texts date from the first century A.D., disclosing oral consumption in herbal tea concoctions, used for pain relieving and sleep inducing. The use of *cannabis* in Hindu India was largely popularized by Shiva smoking the leaf or resin extracts for their psychoactive properties. The use was spread through Arab lands in the Middle Ages, before coming into Europe and the Americas. For centuries, *Cannabis* resin was made by hand rubbing the flowers or sifting with fine cloths as screens.

Cannabinoids are receiving just recently a new and increasing interest again for recreational freedom, State taxes, nutrition and pharmaceutical commercial and industrial purposes.

Glandular trichomes of the *Cannabis Sativa* plant store amounts of cannabinoids, in particular tetrahydrocannabinol (THC) and cannabidol (CBD). Almost all current research focuses either on genetically engineered plants exhibiting enhanced contents of THC, CBD or other molecules, or on medical applications of particular cannabinoids. The known extraction methods are usually dedicated to isolate a specific molecule and thus involve a solvent. For example, US 2013/0079531 (to Barringer) teaches an EtOH extraction at −20° C.

There is to our knowledge very few methods to purify integer glandular trichomes.

U.S. Pat. No. 6,158,591 (to Delp) uses cold water and ice in a wash process to cause the resins to become brittle, while the remaining plant material becomes more flexible. Separation is accomplished using an extractor having a washing chamber and a screen filter disposed above a settling chamber. A collection bottle is placed below, and may include a filter to separate resin particles from the solute. A corresponding device comprising two sieving bags of different mesh size for separating resin particles from various plant material may be found for example under the name of "Ice-O-Later®".

A drawback of the ice-water methods is that some components of the resin material are lost by dissolution in the water. Another drawback of these methods is that the resin must be quickly and carefully dried thereafter to avoid deterioration by fungal growth under moisture. These drawbacks may lead to an alteration of organoleptic properties of the resin.

A dry process is know from the publication of Yerger et al, Plant Physiology, 1992, 99, 1-7, wherein deep frozen plant material are placed together with crushed dry ice ($CO_2$) in a vortex mixer. Glandular trichomes are then separated by sieving. This paper teaches that the dry ice particles act mechanically to separate trichomes from pedicels. Corresponding device may be commercially available under the name of "Pollinator®". Such device comprises a sifting drum accommodating the plant material, tumbling inside a casing, so that the finer fraction of particles fall through the screen around the drum onto the bottom of the casing for later collection. The process is extremely sensitive to the operating parameters such as the temperature, the humidity and the process duration. A very cold and dry atmosphere is required, and short processing time is necessary to recover the resin with a higher purity. Under these conditions, the yield is low.

SUMMARY OF THE INVENTION

The aim of the present invention is therefore to propose a purifying process without the above drawbacks. In particular, it is the aim of the present invention to provide an extraction and purifying process which results both in a high yield and a high purity of isolated glandular trichomes.

The invention proposes a dry process to isolate the glandular trichomes from a glandular trichome-bearing plant material.

The glandular trichome-bearing plant material composes m particular the flowers and the leaves of a plant containing glandular trichomes. Such a glandular trichome-bearing plant material may be for instance the flowers, or the leaves, or a mixture thereof of *Cannabis sativa* plants.

The present process comprises an extraction step of providing a crude trichome powder from the glandular trichome-bearing plant material. Said glandular trichome-bearing plant material is firstly dried and then crushed into a rough plant powder. The resulting rough plant powder is sifted through at least one sieve having a mesh size selected to separate coarser plant contaminants from a finer passing fraction containing the glandular trichomes to be purified, mixed with fine vegetable contaminants. The sift operation may occur under normal seasonal air conditions. Alternatively, the rough plant powder may be frozen at about −20° C. before performing the sifting operation. In another alternative, the rough plant powder may be subject to sequential freezing and thawing cycles before performing the sifting operation.

The resulting fine passing fraction is collected as a crude trichome powder.

The rough plant powder is preferably sequentially sized by means of several sieves having decreasing openings. An example of sifting sequence can comprise a first sift with openings of 200 micrometers, a second sift with openings of 150 micrometers and a third sift with openings of 100 micrometers. It should be understood that any other size of openings may be selected depending on the nature of the plant material. The sequence may also comprise repeated steps with one or more of the opening sizes. The resulting fractions may be combined or collected separately. Each collected fraction may be examined for deciding further processing. Examination of a fraction may be performed by the mean of microscope.

The present process comprises a step of purifying the crude trichome powder to obtain pure glandular trichomes. The crude trichome powder may be obtained by the extraction step above-described or by any other process. This purification step of the crude trichome powder is performed at least partially under frozen conditions at around −20° C. In particular, it comprises the steps of:

a) freezing said crude trichome powder at around −20° C.;
b) Treating said frozen trichome powder by a mechanical operation to shatter the large contaminants into fine dust, while preserving the glandular trichomes to be purified,
c) Sifting said frozen crude trichome powder to separate the fine dust contaminants from the glandular trichomes to be purified, and
d) Recovering said purified glandular trichomes.

Steps a), b) c) and d) may be repeated several times.

Thus, the present process is defined by one or more of the following features and any combination thereof:

Freezing a crude trichome powder, comprising said glandular trichomes and vegetable contaminants, at a temperature equal or below −20° C., Treating said frozen trichome powder by a mechanical operation to shatter the large contaminants into fine dust, while preserving the glandular trichomes to be purified, said mechanical operation comprising one or more of rubbing, vortexing, rolling, and kneading, including any combination thereof, being performed manually or by the mean of a refrigerated crushing equipment, comprising a spinning cage drum and crushing elements such as glass marble, Sifting said crude trichome powder to separate the fine dust contaminants from the glandular trichomes to be purified, comprising placing the crude trichome powder into a refrigerated elongated bag having a calibrated porosity, preferably comprised between 40 micrometers and 50 micrometers, kneading said elongated bag, shaking said elongated bag in such a way that shattered contaminants are expelled out of the bag through the openings thereof, and optionally repeating the above sequence of operations, Allowing the frozen crude trichome powder to warm up until a temperature comprised between 1 and 10° C., preferably around 5° C. before being frozen again, and repeating the previous steps of shattering and siftening between 2 and 10 times, until substantially no fine sieve fraction passes through said sifting means, and Recovering said purified glandular trichomes, The present invention also encompasses a composition comprising glandular trichomes obtained by the process herein described, wherein the glandular trichomes are preferably extracted and purified from *Cannabis Sativa*.

DETAILED DESCRIPTION OF PREFERED EMBODIMENTS

The first step of providing a crude trichome powder obtained from glandular trichome-bearing plant material is described as follows:

Some plant material comprising leaves or flowers or a combination thereof is dried under ambient conditions. The drying phase typically lasts few months, e.g. between one and 5 months. Drying is preferably performed during around two months.

The dry plant material is frozen at around −20° C. (minus twenty degrees Celcius) before being subject to the sifting operations described below. The dry plant may optionally be subject to repeated temperature cycling, being alternatively frozen to around −20° C. and allowed to thaw. The thawing temperature is slightly above 0° C., preferably between 1 and 10° C., more preferably between 3 and 6° C. An ideal thawing temperature is around 5° C. The time to reach the thawing temperature from the frozen state is set to be comprised between 2 and 15 hours, preferably between 3 and 8 hours, and more preferably around 6 hours. This temperature cycling can be repeated a certain number of times, like 2 to 20 times, preferably 5 to 10 times. In a preferred embodiment, the repeating temperature cycling lasts between about 24 hours and about 72 hours continuously. Such a temperature cycling allows ambient humidity to enter the dry plant material. The re-freezing phase thus causes the disintegration of the cell structure comprising all of the contamination. The temperature cycling is sensitive to the humidity rate and may be optimized according to the humidity rate of the environment. Such a temperature cycling is preferably under a humidity rate comprised between about 25% and about 45%.

Whether the plant material has been subject to cycling temperatures or not, it is put into a mesh bag of 250±220 micron openings at a frozen state. The mesh bag may be made of nylon or polyester or any other material having a calibrated porosity. A first fraction of crude trichome powder is expelled from the mesh bag by mechanical means. Such mechanical means includes shaking and impacting with a stick, and may be manual or mechanized.

This first fraction of crude trichome powder is then subject to sifting over a series of frames of concentric mesh sizes. Such frames may be stretched with stainless steel or polyester or any other convenient material. For example, the first fraction of crude trichome powder may be sifted according to the method used to obtain the plant material, while using a 200 micron mesh bag instead of the initial 250±220 micron mesh bag. The same mechanical means as above may be used. In particular, stroke of the plant powder back-and-forth allows the finer particles to pass through the mesh to provide a second fraction of crude trichome powder. While still under the frozen state, the second fraction of crude trichome powder may be subject to a novel sifting operation using a 150 micron mesh bag, under the same conditions as above. The resulting third fraction of crude trichome powder may further be subject to new sifting operation using a 100 micron mesh bag to expel out of the bag a fourth fraction of crude trichome powder.

Each of the second, third and fourth fractions may be subject to an examination before proceeding to the following sifting operation. It may therefore be considered that the second, or the third fraction is of acceptable quality to be involved in the following step of purification of the glandular trichomes. Thus, the extraction process used to produce the crude trichome powder may involve less sifting operations. Alternatively, one or more sifting operation may be repeated once or more times. The examination of the fractions can be performed by the mean of a microscope.

In one embodiment, broken flower parts, are crushed and passed over a series of sieve screens from 200 microns mesh, 150 micron mesh and 100 microns mesh under ambient seasonal air temperatures. The sized fractions thereby obtained are examined under microscope to determine whether some fractions having poor trichome content should be discarded, and whether some fractions should be further treated separately.

The fraction which is recovered for the following step of purification may be conserved at −20° C. or let to warm up to the ambient temperature.

The following step of purifying the glandular trichomes from the crude trichome powder aims at eliminating the vegetable contaminants smaller than the glandular trichomes. The crude trichome powder is preferably obtained by the above-described extraction process, and more preferably wherein temperatures cycling have been applied. However, crude trichome powder resulting from alternative processes may also be used. At this state, sifting the product once more through a sieve having a mesh size corresponding to the size of the smallest glandular trichomes would only eliminate contaminants of already very small size at the origin, leaving all contaminants of intermediate size within the product. The purifying process thus comprises a step of freezing the crude trichome powder, in order to shatter all vegetal contaminants of any original size into a very fine icy dust. The inventor has found that normal cell walled vegetal matter freezes, expands and becomes very fragile to being fractured, at the aforesaid temperature, contrarily to the glandular trichomes, and that mechanical forces applied to frozen crude trichome powder, like rubbing, vortexing, rolling, kneading, etc. are capable to shatter stalks, hairs and the like into fine icy dust while leaving whole the glandular trichomes. Such shattering preferably involves moderate mechanical treatment, which do not destroy nor substantially affect the structure of the glandular trichomes.

Such a moderate mechanical treatment may be performed manually or by the mean of a crushing equipment. A crushing equipment typically comprises a spinning cage drum with a barrel bag. The crushing equipment preferably comprises a casing wherein the spinning cage drum is included, in such a way to recover the material expelled from the spinning cage drum. The spinning cage drum is linked to a rotating means, outside the casing. Said rotating mean may be a manual rotating mean, like a handle, or a motorized rotating mean, like an electrical motor. The crushing equipment preferably comprises a refrigerating mean able to refrigerate the spinning cage drum and its content to a temperature down to −20° C. In a preferred embodiment, the casing of the crushing equipment comprises the refrigerating means, in such a way to define a refrigerated enclosure. In order to crush the vegetable contaminants, the spinning cage barrel is filled with the crude trichome powder in the presence of glass marbles. Such glass marble may be half inch glass beads. The weight ratio between the crude trichome powder and the glass marbles may vary between 2/8 and 8/2. In a preferred embodiment, the weight of the glass marble is close or equal to the weight of the crude trichome powder to be purified. When rotating the spinning cage drum, the frozen glass balls crush the vegetal contaminant of the crude trichome powder, while preserving the glandular trichomes. It is preferable that a temperature of around −20° C. is maintained during the crushing process. As an example, the frozen crude trichome powder may be subject to 100 to 200 minutes of spinning into the spinning cage drum for shattering the cellular based vegetable contaminants.

In case the crushing equipment is not provided with a refrigerating mean, then the spinning drum should be disposable in order to be put into a freezer at −20° C. before initiating the crushing process. Under such conditions, the crushing process should not last too long, and preferably not longer than around 10 minutes, preferably no longer than around 5 minutes, and more preferably no longer than 2 minutes. In case a longer crushing process is necessary, the spinning drum should be put again into the freezer at −20° C. to avoid any significant warming of the content of the spinning drum.

As a preferred equipment, the inventor has selected an equipment combining elongated bags that are made of polyester screen mesh of 45 microns, into which the crude trichome powder is filled and a crushing equipment comprised of a refrigerated support plate and of a pipe or roll. The bag containing the frozen powder is arranged on the plate and knocked forcibly with the pipe. Then the bag is shaken so that shattered fine vegetal material is expelled through the openings of the bag. The shattered icy dust is far finer than 45 microns and through the repeated shaking of the long bag with two hands between repeated shattering impacts all vegetal matter finds it's way out of the bag and when no more dust (icy powder) is seen coming out of the bag after repeated shattering impacts and shaking then all vegetal matter has been removed and the only thing remaining inside the 45 micron bag are the cleaned trichomes having a size comprised between 55 micrometers and 110 micrometers.

The crushing process, shattering the contaminants, is followed by a sifting step, which allows to eliminate the shattered contaminants. The sifting step is performed by the mean of a porous supple recipient like a porous bag, having a calibrated porosity. The porosity of the bag is selected in accordance to the size of the glandular trichome to be purified. As a range, indoor *Cannabis saliva* hybrids are making large glands from 90 to 110 microns. On the same plants outdoor landrace, glands might range from 60 to 90 microns. For the indoor glandular trichomes, a screen bag having a porosity of around 73 micron may be used. For outdoor glandular trichomes a 45 micron sieve is better optimized.

An amount of up to 250 to 500 grams of crude trichome powder may be put into a a 45 micrometers mesh polyester barrel bag of around 13 litters.

The sequence of shattering and sifting may be repeated several times up to completion, until no more icy dust is expelled from the sifting bag. In such a way glandular trichomes substantially free from vegetable components of poor value are obtained.

While the shattering and sifting sequence is performed at a substantially constant freezing temperature of around −20° C., the inventor has found that repeated freezing, short thawing and re-freezing of the crude trichome powder to be purified, allows the cellular structured matter in the contaminating vegetal matter to expand and disintegrate more rapidly and thus shatter more rapidly and more thoroughly, necessitating less impacting by crushing means. Further, the re-freezing step provides more accurate temperature control and also provides more freedom concerning the total operating time since the re-frozen material may be processed as well immediately or stored for a desired time before the next cycle.

The sequence of shattering and sifting may thus comprise an additional step of thawing. The freezing-thawing cycle may occur independently of the operations of shattering and sifting. Alternatively, the thawing phase may be combined to the shattering process. In other words, the frozen crude trichome powder is introduced to the spinning drum and rotated for a given duration while being allowed to thaw, and then frozen again.

EXAMPLE 1

50 kilos of flowers of outdoor *Cannabis sativa* plants were cut and two months dried, and then crushed into a rough plant powder. A sample of the powder of the flowers to be treated was sized and examined with a microscope for establishing the upper and lower screen sizes. Here we have passed our rough powder through the 220 nylon bag then carded it over a 200 µmicron stretched frame, followed by a 150 µmicron frame and finally a 100 µmicron screen stretched frame. This process can happen in normal seasonal air temperatures but is better taken to −20° C. A 100 µmicron mesh size was selected for the sift screen, the trichomes being smaller than 110 µ. Sifting said rough plant powder through a sieve having a mesh size of a 100 microns produces a crude powder comprising the glandular trichomes and ever present debris of plant and leaf matter and pistelite hairs. Then the crude powder is put into a spinning barrel bag having 45 micron openings.

Once the crude powder is filled into the 45 micron mesh bag, it is put to hang in at −20° C. air to become freeze dried, as are all of the utensils. If using an electric spinning drum with the 45 micron barrel bag inside place the spinner into a chest freezer at −20° C. for 100 to 200 minutes. If using the manual method in the out doors in winter, again and again all through the process the screen bag is given a shake by holding onto the top and bottom of the bag and, like softly clapping hands, extending and compressing the bag causes air to be pulled into and be expelled from the bag taking with it fine dust. The purpose of agitating the bag is to expel fine contaminant dust from the bag. After shaking, the bag is put onto a refrigerated flat stone plate and impacted with a pipe; thereafter the barrel bag is shaken again. These two steps are repeated several times, progressively by repeated shattering impacts all vegetal matter is reduced to icy dust. When all vegetal matter has found it's way out of the bag and when no more dust is seen coming out of the bags after repeated shattering impacts and shaking then all vegetal matter has been removed and the only thing remaining inside the 45 micrometers all screen bag are the 100% cleaned trichomes of between 55 and 110 microns. The whole, intact and undamaged trichomes found in the screen bag are not smaller than 45 micrometers and do not pass through the 45 mesh of the bag. The yield is over a kilo of purified canabis trichomes.

EXAMPLE 2

A 45 micrometers barrel bag filled with trichome powder is frozen for six hours at −20° C., and then removed from the freezer and immediately shaked and claped by hand for one minute. Then the bag is allowed to hang in a cool dehumidified room wherein the humidity is comprised between around 25% and around 45% at 5° C., thawing and collecting condensation for five minutes before returning it to the freezer for six hours at −20° C. with an active humidity extraction ventilation. A normal ventilated chest freezer running at Super-Cold is appropriate thereto.

The sequence of freezing, thawing and shattering is repeated six times, until the trichome powder can be seen to be pure in a microscope. This embodiment of the process makes it possible to work from a freezer within 24 hours or slightly more, instead of processing the powder by forceful impacting/shattering within a few hours without a process stop at a temperature that possibly cannot be maintained constantly at −20° C.

Considering the micron size of the icy dust going out of the bag at −20° C. as set forth above, the 45 micron mesh bag is perfect, but no matter to the process, these numbers of microns are from actual use in the experiments, but in fact other sizes for the lower screen doing the holding of the desired glands while allowing the contaminants to exit could be used. Also another sized screen could be used as an intermediate screen to achieve more detailed separation, if desired. Finally, the mesh size of the bag is selected according to the plant material to be processed.

Finally, it is to be noted that the glandular trichomes purified by the process according to the present invention provide a different organoleptic taste and smell as compared to

- trichomes isolated by a dry process of the prior art, since the latter still contain vegetal contaminants impacting the organoleptic properties upon consumption,
- trichomes isolated by a wash process of the prior art, probably since in the latter some soluble components have been washed out.

The invention claimed is:

1. A dry process for isolating clean glandular trichomes from a trichome bearing plant powder, comprising the steps of:
    a) freezing a crude trichome powder, comprising said glandular trichomes and contaminants, at a temperature equal to or below −20° C.,
    b) treating said frozen trichome powder by a mechanical operation to shatter the contaminants into fine dust contaminants, while maintaining said crude trichome powder at a temperature equal to or below −20° C. and while preserving the glandular trichomes to be purified,
    c) sifting said crude trichome powder to separate the fine dust contaminants from the glandular trichomes to be purified while maintaining said crude trichome powder at a temperature equal to or below −20° C., wherein the sifting of the frozen crude trichomes comprises substeps, comprising:
        c1) placing the crude trichome powder into a refrigerated elongated bag having a calibrated pore size,
        c2) impacting said elongated bag for shattering the contaminants into fine dust,
        c3) shaking said elongated bag in such a way that the fine dust contaminants are expelled out of the bag through the openings thereof, and
        c4) repeating steps c1, c2) and c3) until no more fine dust contaminants are expelled from the elongated bag; and
    d) recovering said purified glandular trichomes while still frozen at a temperature equal to or below −20° C.

2. The dry process according to claim 1, further comprising:
    repeating the mechanical operation to shatter the contaminants into fine dust contaminants, and
    repeating the shaking of said elongated bag to further expel the fine dust contaminants.

3. The dry process according to claim 2, wherein said mechanical operation is performed manually at a temperature equal to or below −20° C. by means of a refrigerated crushing equipment, comprising a spinning cage drum and crushing elements.

4. The dry process according to claim 1, wherein the impacting process of step c2) is kneading performed at a temperature equal to or below −20° C. by means of a pipe or a roll, while the elongated bag lies on a refrigerated plate.

5. The dry process according to claim 1, wherein said pore size is between 40 micrometers and 50 micrometers.

6. The dry process according to claim 1, wherein the plant powder comprises powder of flowers of *Cannabis sativa*.

7. The dry process according to claim 3, wherein the crushing elements comprise glass marbles.

8. The dry process according to claim 5, wherein the pore size is approximately 45 micrometers.

* * * * *